United States Patent
Prause

(10) Patent No.: US 6,935,178 B2
(45) Date of Patent: Aug. 30, 2005

(54) DEVICE FOR INSPECTING PIPES USING ULTRASOUND

(75) Inventor: Reinhard Prause, St. Augustin (DE)

(73) Assignee: GE Inspections Technologies Systems GmbH (DE)

( * ) Notice: Subject to any disclaimer, the term of this patent is extended or adjusted under 35 U.S.C. 154(b) by 0 days.

(21) Appl. No.: 10/488,156

(22) PCT Filed: Jul. 18, 2002

(86) PCT No.: PCT/DE02/02639
§ 371 (c)(1),
(2), (4) Date: Feb. 27, 2004

(87) PCT Pub. No.: WO03/027664
PCT Pub. Date: Apr. 3, 2003

(65) Prior Publication Data
US 2004/0211261 A1 Oct. 28, 2004

(30) Foreign Application Priority Data
Aug. 29, 2001 (DE) .......................... 101 41 768

(51) Int. Cl.[7] .............................................. G01N 29/04
(52) U.S. Cl. ...................................................... 73/622
(58) Field of Search .......................... 73/622, 623, 620

(56) References Cited

U.S. PATENT DOCUMENTS 3,107,521 A * 10/1963 McClure ....................... 73/640
3,358,497 A * 12/1967 Hauk ............................ 73/49.1
3,828,609 A * 8/1974 Furon et al. ................... 73/622
3,877,293 A * 4/1975 McKeage ..................... 73/49.1
4,246,794 A   1/1981 Sheets et al. ................... 73/622

FOREIGN PATENT DOCUMENTS

DE  38 03 151 A1   8/1989
EP  0 398 002 A1  11/1990
WO  WO 02/35226 A1  5/2002

* cited by examiner

Primary Examiner—Hezron Williams
Assistant Examiner—Rose M. Miller
(74) Attorney, Agent, or Firm—Akerman Senterfitt

(57) ABSTRACT

The invention relates to a device for inspecting pipes using ultrasound, in particular for inspecting the end regions of a pipe. Said device comprises at least one ultrasonic inspection head (38) with an inspection tank (24), which a) has a receiving chamber (26) that is designed to receive a coupling fluid, in particular water (27), b) forms an axial passage through which a pipe (20) that is to he inspected can be transported along an inspection line (28) relative to the inspection tank (24) c) has sealing elements at the front and rear (34, 36), said elements being adapted to the external diameter of the pipe (20) that is to be inspected and delimiting the receiving chamber (26), and d) contains the inspection head(s) (38) in such a way that only coupling fluid is present between the inspection head (38) and the pipe (20) that is to be inspected. The device also comprises a cylindrical mandrel (22), whose external diameter is adapted to the external diameter of the pipe (20) to be inspected and which has a front seal (42) on its front face that forms a tight seal with a first front face of the pipe (20) to be inspected. The length of said mandrel is greater than the clearance between the two sealing elements (34, 36).

9 Claims, 3 Drawing Sheets

DEVICE FOR INSPECTING PIPES USING ULTRASOUND

Figure 1:
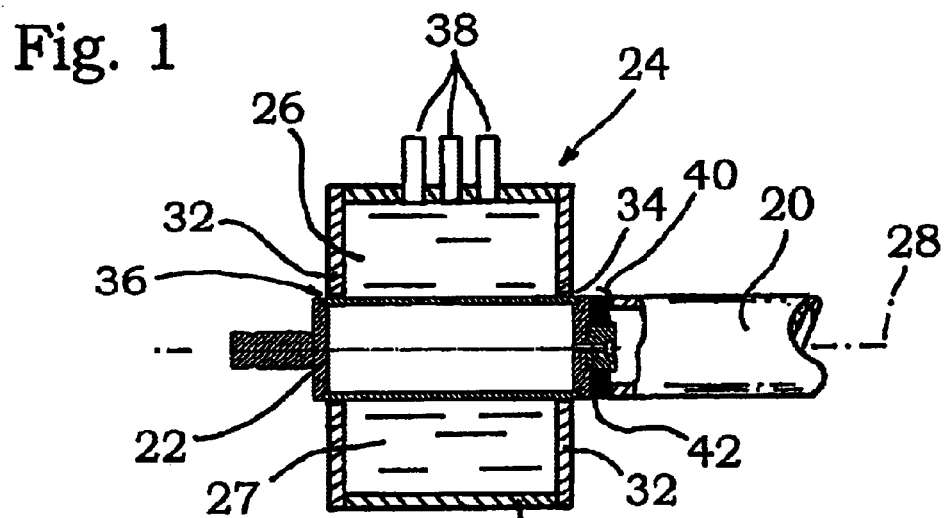

The present invention relates to a device for inspecting pipes using ultrasound comprising at least one ultrasonic probe and an inspection tank which a) has a receiving chamber for receiving a probe-to-specimen contact liquid, in particular water, b) defines an axial passage through which a pipe that is to be inspected can be transported along an inspection line relative to the inspection tank, c) is provided with front-side and rear-side sealing means which are adapted to the external diameter of the pipe that is to be inspected and which delimit the receiving chamber, and d) receives the at least one probe so that probe-to-specimen contact liquid is only found between the probe and the pipe that is to be inspected.

Such a device for the inspection of pipes is known from PCT/DE 00/03747. It is further known from the DE-Book J. and J. Krautkraemer, Material Testing with Ultrasound, Springer Verlag (Publishing House), fifth edition.

It is not possible to inspect the entire pipe with the devices of the prior art. Uninspected portions remain always at the front and at the end portion typically having a length of 50–200 mm. In order to be able to manufacture pipes that are inspected completely, i.e. over their entire axial length, the uninspected portions must, in conformity with prior art, be cut off.

This is a disadvantage. The cutting-off of uninspected end portions of a pipe means a considerable loss.

With a view to avoiding uninspected pipe end portions that have to be cut off, it has already been proposed to include the pipe ends in the inspection. In this connection, the problem of sealing the open pipe ends arises. Great care must be taken to ensure that the inner walls of the pipe that is to be inspected remain dry. Even small quantities of water inside the pipe, for instance one drop, would affect the ultrasonic inspection, they provide false ultrasound signals at the place wetted by water.

The risk as described above does not exist with solid material. Nevertheless, an inspection of solid material using the devices of prior art is not possible without any problem. For the inspection, the receiving chamber of the inspection tank must always be filled with an adequate amount of probe-to-specimen contact liquid.

Bars that are to be inspected, whether they are pipes or solid material, must be inserted into the inspection tank along the horizontal inspection line so that the same may pass through the receiving chamber along the axial passage. The axial passage must, however, be sealed somehow at its two ends to prevent that probe-to-specimen contact liquid leaks there all the time. The rear-side sealing means are suited for adhering to the external circumference of the bars that are to be inspected. It does not suffice to seal the passage in the direction of the inspection line in a manner which is adequate for always retaining sufficient probe-to-specimen contact liquid in the receiving chamber.

What matters is therefore not an exact sealing between the sealing means and the bars that are to be inspected, a certain gap may well remain between sealing means and pipe provided that probe-to-specimen contact liquid does not leak in such a quantity that a required water level in the receiving chamber can no longer be maintained.

This is where the present invention comes in. Its object is to improve the device for pipe inspection of the type mentioned in the beginning so as to make an inspection of end portions possible.

Proceeding from the device of the type mentioned in the beginning, this object is achieved by providing a cylindrical mandrel the external diameter of which is adapted to the external diameter of the pipe that is to be inspected which has a front-side sealing by which it is in sealing contact with a first front side of the pipe that is to be inspected and which has a length that is greater than the clearance of the two sealing means.

It is a fact that the invention is preferably suited for the inspection of pipes, it is, however, as a general rule, suited for the inspection of bars, i.e. also for the inspection of solid material. It is preferably suited for round material, but is equally well suited for prismatic bodies of all kind, i.e. bodies with a constant cross-section over their length.

The mandrel has the same cross-section as the test piece, i.e. in particular the same external diameter as the pipe that is to be inspected. It is the task of the mandrel to seal off the inspection tank to the outside, i.e. when no inspections are made and also during inspections. The mandrel lengthens so to speak the test piece in the axial direction, i.e. in the direction of the inspection line thereby shifting the site where no inspection can be made to the region of the mandrel. It is now no longer in the end portion of the test piece, i.e. of the pipe that is to be inspected.

Before an inspection is started, the mandrel fills out the passage. Thereby, the required quantity of probe-to-specimen contact liquid can be maintained in the inspection tank, and the amount of probe-to-specimen contact liquid that is lost through the two sealing means can be easily replaced by means of a pump. When the inspection is started, at first a tight connection between the pipe that is to be inspected and the mandrel is made outside of an inspection tank. This ensures that the end portion of the pipe that is to be inspected is tightly sealed. In this state, the end portion of the pipe that is to be inspected is now inserted into the inspection tank where the inspection can take place. The pipe that is to be inspected enters the inspection tank through the front-side sealing means. In the course of the inspection it is transported until it reaches the rear-side sealing means. Now, the mandrel is actually no longer required. The pipe can be transported even further, and the inspection can be continued over the entire length of the pipe. In order to be able to inspect the rear-end portion, a mandrel is also required there.

Alternatively, only the front-side end portion of the pipe is inspected, and with devices of the prior art which are separately provided for the inspection of the pipe end, an overlapping inspection of the area between the end portions is carried out. In this context, it is advantageous to provide for each pipe end a separate device for the pipe end inspection.

The advantage of the device according to the present invention is that end portions of a pipe can be reliably inspected and that, optionally, also the main section is inspected or only an end-portion inspection is performed. The sealing of the inspection tank by the mandrel is always ensured. This makes it possible to use different types of inspection tanks for the invention. For example, the inspection can be performed according to the so-called "puddle technology" where only a part of the pipe is immersed in the probe-to-specimen contact liquid and where the inspection can be made from below, from the so-called six o'clock position. It is, however, also possible to use inspection tanks into which the pipe that is to be inspected is fully immersed, i.e. where the entire outer wall of the pipe is wetted. It is in particular devices according to the aforementioned PCT/DE 00/03747 which are well suited for this purpose. It is also possible to use a rotating tank as is known for instance from DE 4 410 580 A.

In an advantageous improvement of the invention, the two sealing means are removably attached to the inspection tank. This makes it possible to select and to employ the respective appropriate sealing means for the respective pipe that is to be inspected.

In a preferred development of the invention, the mandrel is provided with a holding device at its other front side. This holding device for the mandrel is to be provided with a clamping device. The clamping device interacts with the holding device. In this manner, the mandrel can be held and manipulated by means of the holding device. Furthermore, different types of mandrels can be used, i.e. mandrels with different cross-sections and/or different external dimensions.

In a preferred improvement of the invention, the holding device of the mandrel is arranged movably relative to the inspection tank in the direction of the inspection line. This makes it possible to move the pipe relative to the inspection tank. As a general rule, either the inspection tank can be arranged movably in the direction of the inspection line and/or the pipe can be arranged movably in the direction of the inspection line.

In a preferred improvement of the invention, the holding device can be arranged rotatably around the inspection line. In this manner, the mandrel can be rotated together with the pipe that is to be inspected which is coupled to it. Such a rotation is, for instance, required for the inspection according to the puddle technology when the entire circumference of the pipe is to be inspected. An inspection using a rotating water jacket does not require a rotation of the pipe that is to be inspected.

Moreover, it has proved to be an advantage that the clamping device exercises in the direction of the inspection line an axial force on the mandrel with a biasing device associated with the holding device being provided for that purpose. The pipe that is to be inspected is held in a transport device in such a manner that an axial force can be exerted on the pipe that is to be inspected. By means of the biasing device, the front-side sealing of the mandrel is pressed against the first (facing) front side of the pipe that is to be inspected in such a manner that a tight sealing is accomplished. In this manner, water is prevented from entering the inside of the pipe.

Alternatively, the front-side sealing can also be implemented so that it can be expanded in the radial direction thereby closely adhering to the inner surface of the end portion of the pipe that is to be inspected. Here, an inflatable seal can, for instance be used, such as a cylindrical sealing pad or a normal pipe seal pad.

In a preferable improvement of the invention, the height of the holding device can be adjusted vertically and thus transversely to the inspection line relative to the inspection tank. In this way, the height of the holding device can either be adjusted relative to the inspection tank which is of advantage when inspections are made using the puddle technology or, alternatively, the inspection tank can be adjusted vertically relative to the holding device.

Last but not least, it has turned out to be advantageous that the pipe that is to be inspected is held in a transport device which, on the one hand, facilitates transportation of the pipe axially to the inspection line and, on the other hand, rotation of the pipe around the inspection line and thus around its pipe axis. This reduces the mechanical demands on the inspection device as such.

Figure 2:
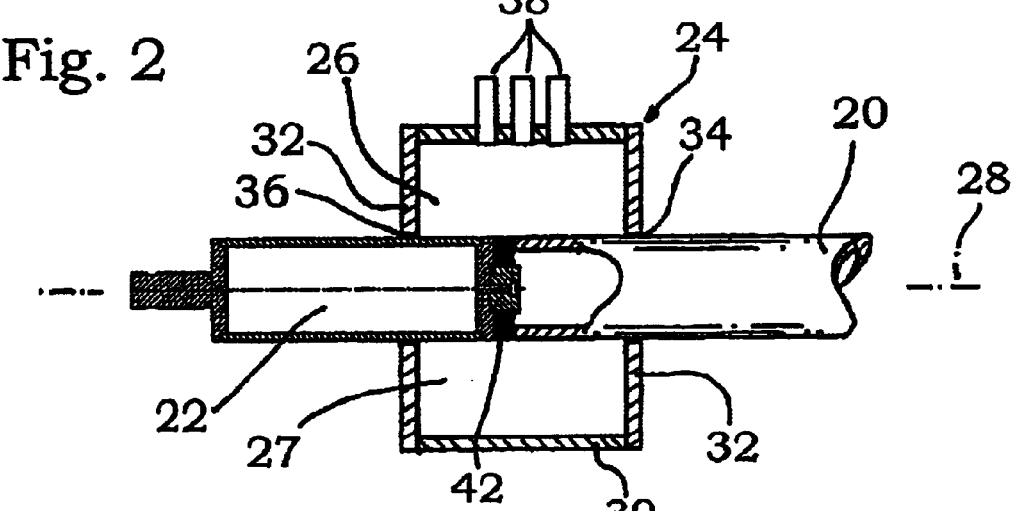
Figure 3:
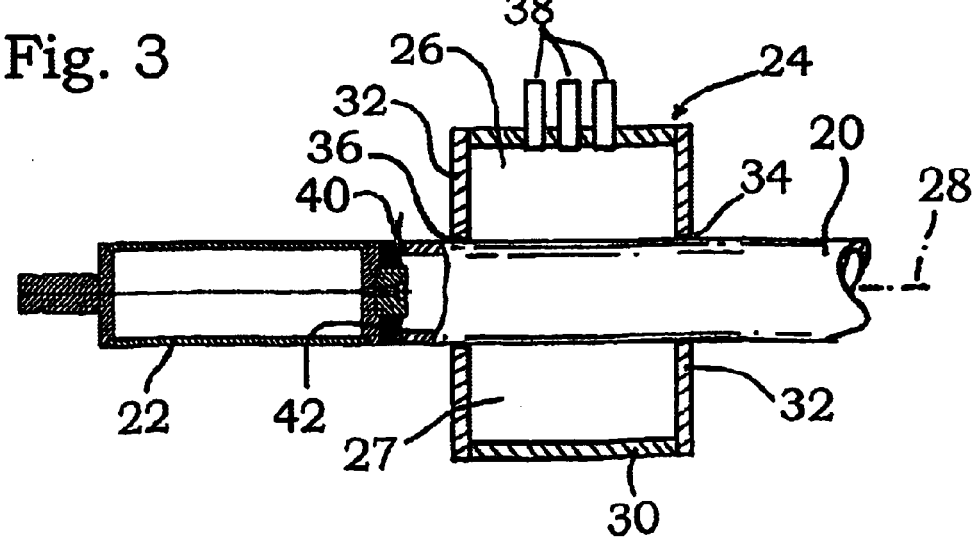
Figure 4:
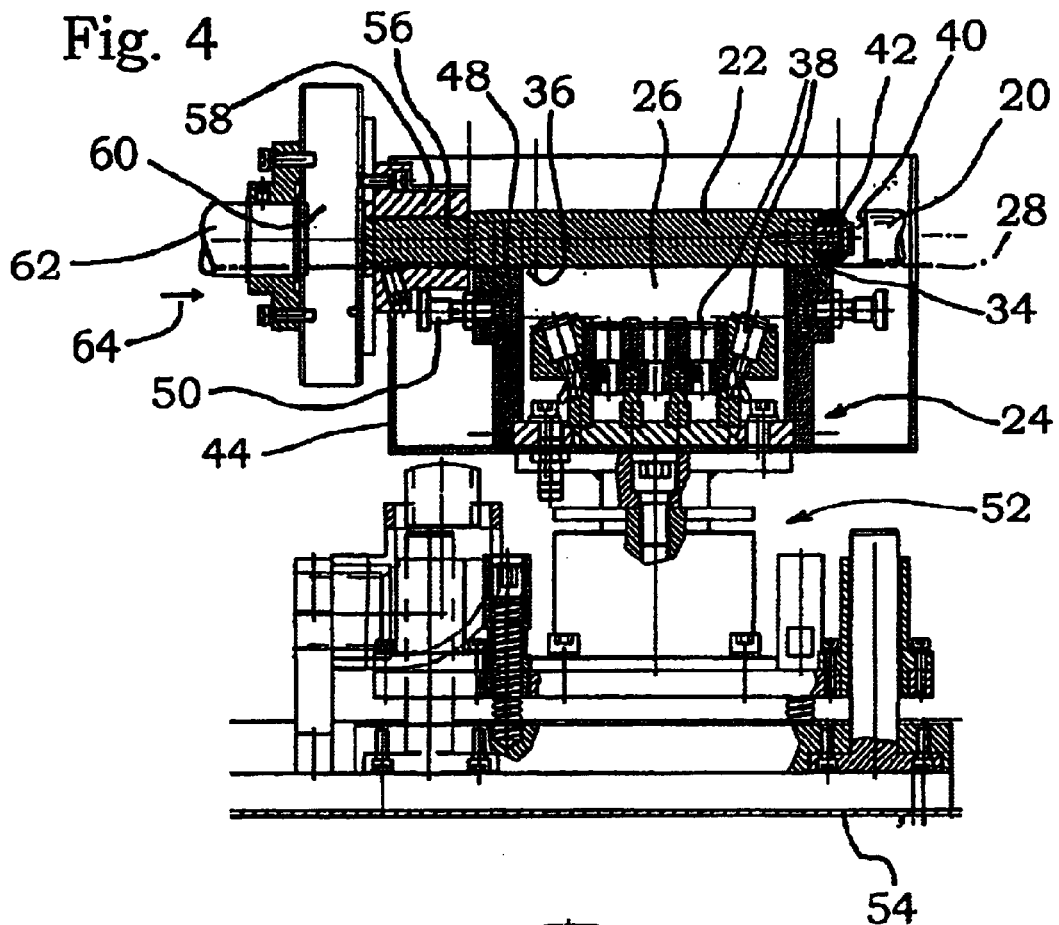
Figure 5:
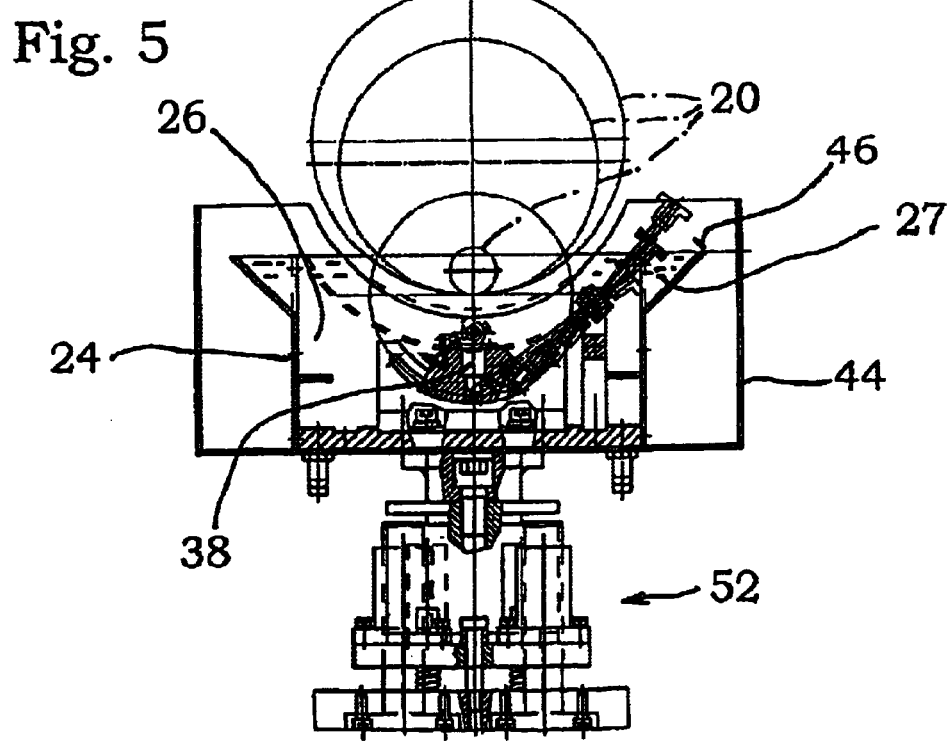
Figure 6:
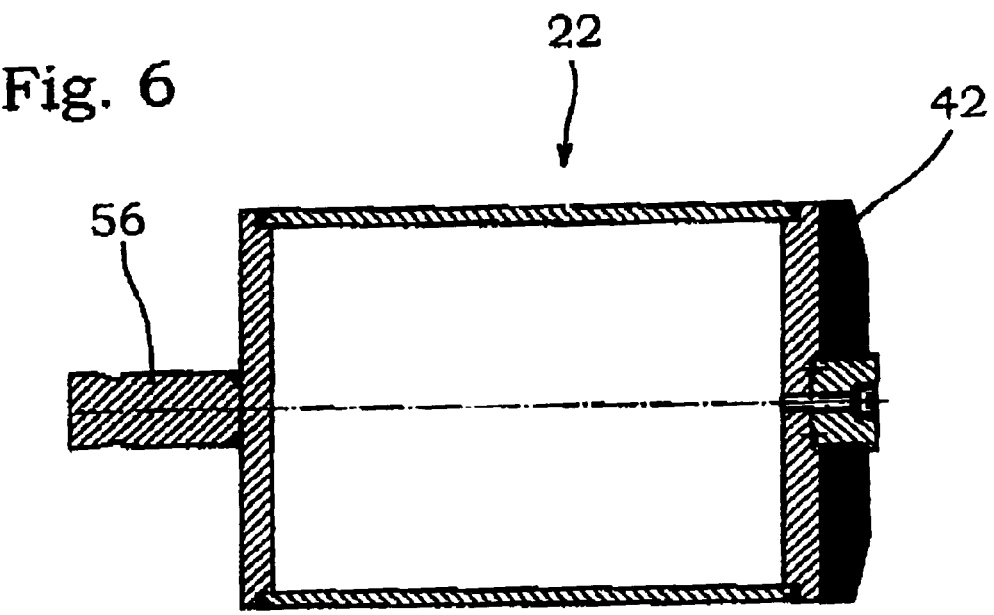
Figure 7:
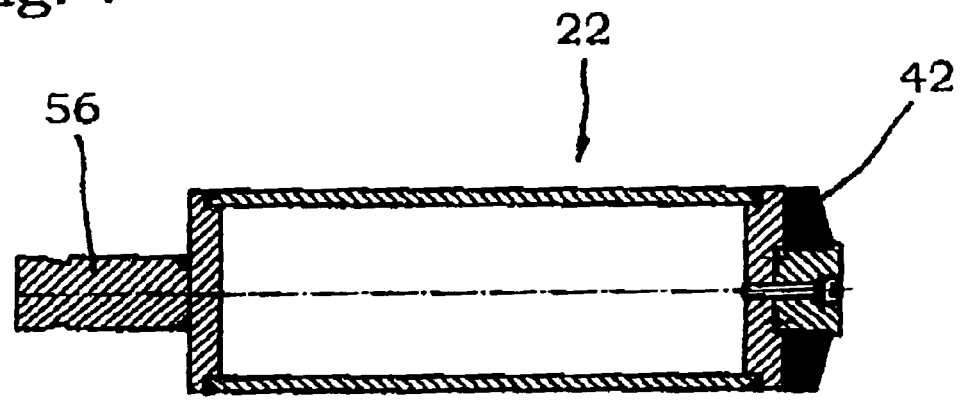

Additional advantageous features of the invention result from the other claims as well as from the following description of embodiments of the invention which shall not be understood as being restrictive. They are described hereinafter with reference also to the drawings in which:

FIG. 1 is a partially sectional side view of a device for pipe inspection using ultrasound showing the state where a cylindrical mandrel is located within the inspection tank axially closing the same, FIG. 2 is an illustration as in FIG. 1 which, however, now shows the state where a connection point between the mandrel and a pipe that is to be inspected is located within the inspection tank, FIG. 3 is an illustration as in FIG. 1 which, however, now shows the state when the connection point between the mandrel and the pipe that is to be inspected has passed the inspection tank with only the pipe that is to be inspected remaining within the inspection tank, FIG. 4 is a side-view similar to FIG. 1 of a device working according to the puddle technology showing, as in FIG. 1, the state where the mandrel axially closes the inspection tank, FIG. 5 is a cross-section of the arrangement according to FIG. 4, FIG. 6 is a sectional view of a mandrel with a comparatively large diameter, FIG. 7 is a sectional view of a mandrel as shown in FIG. 6, here with a smaller diameter.

The first embodiment according to FIGS. 1 to 3 shows a pipe 20 the end portion of which is to be inspected using ultrasound. This end portion is in direct and sealing contact with a mandrel 22 which has the same external diameter. This mandrel is located within an inspection tank 24 which delimits a cylindrical receiving chamber 26. The receiving chamber 26 is completely filled with water 27. The inspection tank 24 defines an axial passage for pipe 20 that is to be inspected and mandrel 22 coupled to the pipe. The passage is centred, just as inspection tank 24, around an axis 28 which is hereinafter referred to as inspection line. It is shown as a dot-dash line.

Inspection tank 24 consists essentially of a cylindrical casing 30 and two side rings 32 which are, on the one hand, detachably connected to casing 30 and, on the other hand, tightly connected to the same. Each of them has a centric passage for pipe 20 and/or mandrel 22 and there, within the area of the passage, sealing means 34 and/or 36. These sealing means 34, 36 define the axial passage.

Within casing 30, ultrasonic probes are arranged so that they face the inspection line with their active area. Between these ultrasonic probes and pipe 20 and/or mandrel 22, there is only probe-to-specimen contact liquid, i.e. water 27.

In a first embodiment, inspection tank 24 rotates around axis 28, such pipe inspection devices being known for instance from the aforementioned DE-Book. In another embodiment, inspection tank 24 is stationary and the water jacket located within the receiving chamber 26 rotates around pipe 20 and/or mandrel 22. Such devices are known from the aforementioned PCT/DE 00/03747.

Pipe 20 that is to be inspected is transported along inspection line 28 as will be described below:

For this purpose, pipe 20 is held at its right end portion (not shown) and moved axially. Mandrel 22 is also held in such a way that it can move axially. Between mandrel 22 and pipe 20, a force is exerted in an axial direction which presses a first face 40 of pipe 20 to a front-side face of mandrel 22 which is provided with a seal 42 on the face. This seal is made for instance of rubber or of another elastic material. It has a bevelled conical front area in order to achieve a line contact with the first face 40 of pipe 20. A sealing which prevents the entry of water into the inside of pipe 20 is essential. The configuration of the front-side seal 42 is optional as long as it serves the purpose of sealing against the first front side 40.

In the state as shown in FIG. 1, mandrel 22 fills out completely the axial passage of inspection tank 24. In this state, it is only mandrel 22 which prevents the flowing out of water at the holes which are defined by sealing means 34, 36. In this state it is, therefore, of no importance whether a pipe 20 is connected with mandrel 22 or not. Consequently, the state according to FIG. 1 is the resting position of the inspection device. As a general rule, it is possible to carry out an ultrasound inspection already in the state as shown in FIG. 1. In this case, mandrel 22 would be inspected.

It is in particular shown in FIG. 1 that mandrel 22 is longer than the axial passage so that it can fill out the passage on both ends. Mandrel 22 has the same external dimensions as the pipe that is to be inspected. If, for instance, a pipe 20 with a hexagonal external cross-section is to be inspected, mandrel 22, too, is hexagonal at its outer surface. Then, also the sealing means 34, 36 are arranged on a hexagonal line.

If a bar is to be inspected instead of a pipe 20, the sealing is of no relevance, i.e. front-side sealing 24 is not required. In this case, too, the external cross-section of mandrel 22 must be in conformity with the external cross-section of the bar that is to be inspected. Here, too, both of them must be arranged equiaxially.

In the state according to FIG. 2, the combination of pipe 20 and mandrel 22 has been shifted a bit to the left so that the contact point of pipe 20 and mandrel 22 is now located within the receiving chamber 26. The arrangement is such that the right one and the central one of the three probes 38 which are shown can already inspect the end portion of pipe 20 while the left one of the three probes 38 still meets mandrel 22. This shows that pipe 20 can be inspected up to its first face 40 without any portions remaining uninspected. During the inspection, pipe 20 is transported to the left together with mandrel 22. FIG. 2 shows a state where the front-side sealing means 34 is in contact with pipe 20 while the rear-end sealing means 36 is still in contact with mandrel 22.

FIG. 3 now shows a state where pipe 20 that is to be inspected completely fills out the axial passage of receiving chamber 26 and an already inspected end portion of pipe 20 projects from inspection tank 24. In this state, mandrel 22 is, as a general rule, no longer required. It is pipe 20 alone that seals the receiving chamber 26 to the outside. It is apparent that pipe 20 when it is transported further to the left can be inspected over its entire length up to a right end portion which is not shown here. If a mandrel 22 is attached to the right end portion, too, the right end portion can also be inspected in the course of the same passage.

If the device according to FIGS. 1 to 3 is to be adapted to a pipe 20 or to a bar with a cross-section other than that of pipe 20 that is shown here, the side rings 32 or only a part of these side rings 32 which comprises the sealing means 34, 36 are/is replaced. Furthermore, mandrel 22 is replaced. After the filling of receiving chamber 26 with water, the inspection can begin. It is also possible to shift inspection tank 24 relative to pipe 20 thereby making transportation of pipe 20 in axial direction unnecessary. Pipe 20 can also be rotated around axis 28.

The embodiments according to FIGS. 4 and 5 are dealt with below. In particular those features are described which differ from the first embodiment which was discussed and shown herein in principle.

In the second embodiment, pipes or other prismatic bodies are inspected by means of the so-called puddle technology. Here, the probes 38 must necessarily be located below the pipe 20 that is to be inspected. They are arranged in a trough which is open at the top and defines here inspection tank 24. It is surrounded by a collecting trough 44 which has walls that are higher than those of inspection tank 24. The collecting trough 44 is designed in such a way that it collects all water 27 which flows over a top edge 46 of inspection tank 24. Top edge 46 defines at the same time the water level up to which inspection tank 24 is filled with water.

Inspection tank 24 is defined in the direction of inspection line 28 by interchangeable connecting portions 48. For their exchange, a screw 50 must be removed for each of them. These connecting portions 48 support the sealing means 34 and/or 36. The connecting portions 48 have a U-shaped recess open at the top for receiving pipe 20 and/or mandrel 22.

Contrary to the embodiment according to FIGS. 1 to 3, inspection line 28 is now defined by the lowest casing line of pipe 20 and/or of mandrel 22. By this definition, inspection line 28 does not change when the diameter of mandrel 22 and/or of pipe 20 changes. This is apparent from FIG. 5 where three different outer diameters of pipes are shown as a dash-dot-line.

As in FIG. 1, in FIG. 4 it is the mandrel 22 alone that closes inspection tank 24 axially, i.e. in the direction of the inspection line. In this state, a pipe 20 can now be coupled to mandrel 22 without a loss of probe-to-specimen contact liquid. FIG. 4 shows a pipe 20 which has not yet got into contact with mandrel 22.

A total of five probes 38 are provided to which different tasks are assigned. They can be shifted to a certain extent around the six o'clock position by means of a shifting device which is not described in detail since it is prior art.

Inspection tank 24 with its collecting trough 44 is arranged on an absorbing supporting frame 52 which need not be described here in greater detail since it is prior art.

This supporting frame 52 is in turn arranged on a table 54. This table can be stationary, it can, however, also be movable in the direction of the inspection line and/or vertically adjustable.

Mandrel 22 is provided at its left end portion with a clamping area 56 with a clamping recess. This clamping area 56 is surrounded by a holding device 58. This in turn is revolvingly joined with an equalising device 60. This equalising device 60 contains an eccentric coupling. In this way, the axis of pipe 20 and/or of mandrel 22 may move away to a certain extent from the ideal line of a completely cylindrical body without resulting in a change on the other side of the equalising device 60.

The inspection is performed as in the discussed embodiment pursuant to FIGS. 1 to 3. The left side of the equalising device 60 is provided with a guide rod which due to the effect of the equalising device 60 has a stationary axis of revolution. A biasing device can act on it exerting a force to the right as indicated by arrow 64. In this way a force is provided which presses mandrel 22 against pipe 20 and causes a sealing within the area of the front-side seal 42.

Guide rod 62 is held in a frame which is not shown here. Within the same, it can be turned and axially shifted in the direction of inspection line 28. In addition and whenever necessary, it can also be vertically adjusted. On the guide rod 62 or on a rod parallel to it, adjustable projecting parts can be provided which are arranged in a fixed distance to the point where the ultrasonic rays of the probes 38 impinge pipe 20. In this way, a clear allocation to the position of the probes is provided and the inspection can be started when the transition area between mandrel 22 and pipe 20 is above the respective probe 38.

FIGS. 6 and 7 show two different mandrels. Mandrel 22 of FIG. 6 is comparatively thick. The clamping area 56 remains the same. Mandrel 22 according to FIG. 7 has a clearly smaller cross-section than the mandrel shown in FIG. 6. The total length of the different mandrels 22 remains constant but this is not a must. The length of mandrels 22 must just suffice for being able to seal the two end portions of inspection tank 24.

What is claimed:

1. A device for the inspection of end portions of a pipe comprising:
   at least one ultrasonic probe;
   an inspection tank which
   a) has a receiving chamber for receiving a probe-to-specimen contact liquid,
   b) defines an axial passage through which a pipe that is to be inspected can be transported along an inspection line relative to the inspection tank,
   c) is provided with front-side and rear-side sealing means which are adapted to the external diameter of the pipe that is to be inspected and which delimit the receiving chamber, and
   d) receives the at least one probe so that probe-to-specimen contact liquid is only found between the probe and the pipe that is to be inspected;
   a cylindrical mandrel the external diameter of which is adapted to the external diameter of the pipe that is to be inspected which has a front-side sealing by which it is in sealing contact with a first front side of the pipe that is to be inspected, which has a length that is greater than the clearance of the two sealing means, and which is provided with a clamping area at its other front side; and
   a holding device is provided for the mandrel and comprises a clamping device which interacts with the clamping area of the mandrel.

2. A device according to claim 1 characterized in that the inspection tank is a trough which is open at the top and is filled with probe-to-specimen contact liquid up to a liquid level and that the pipe that is to be inspected is partly immersed in the probe-to-specimen contact liquid and the pipe axis remains above the liquid level.

3. A device according to claim 1 characterized in that the inspection tank is a closed container which is filled with probe-to-specimen contact liquid and that the outside of the pipe that is to be inspected is completely surrounded by probe-to-specimen contact liquid.

4. A device according to claim 1 characterized in that the sealing means are detachably arranged at the inspection tank.

5. A device according to claim 1 characterized in that the holding device is arranged movably relative to the inspection tank in the direction of the inspection line.

6. A device according to claim 1 characterized in that the holding device and with it the mandrel are rotatably arranged.

7. A device according to claim 1 characterized in that the holding device comprises a biasing device which exerts an axial force on the mandrel in the direction of the inspection line, that the pipe that is to be inspected is held in a transportation device and that the front-side sealing of the mandrel is pressed by the axial force against the first front side of the pipe that is to be inspected in such a manner that a tight sealing is achieved.

8. A device according to claim 1 characterized in that the height of the holding device is adjustable vertically and thus transversely to the inspection line relative to the inspection tank.

9. A device according to claim 1 characterized in that the pipe that is to be inspected is held in a transportation device which, on the one hand, facilitates transportation of the pipe in the direction of the inspection line and, on the other hand, rotation of the pipe around its pipe axis.

* * * * *